(12) United States Patent
Basford et al.

(10) Patent No.: US 12,198,800 B2
(45) Date of Patent: Jan. 14, 2025

(54) SYSTEMS, DEVICES, AND METHODS FOR MANAGING OPERATION OF DIAGNOSTIC TESTING INSTRUMENTS

(71) Applicant: IDEXX Laboratories, Inc., Westbrook, ME (US)

(72) Inventors: Eric Christopher Basford, Scarborough, ME (US); Jason Bowie, Raymond, ME (US); Craig Taylor Davis, Peaks Island, ME (US); Keith Douglass, Scarborough, ME (US); Regina Hyson, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 884 days.

(21) Appl. No.: 17/108,400

(22) Filed: Dec. 1, 2020

(65) Prior Publication Data

US 2021/0174942 A1 Jun. 10, 2021

Related U.S. Application Data

(60) Provisional application No. 62/943,587, filed on Dec. 4, 2019.

(51) Int. Cl.
*G16H 40/20* (2018.01)
*A61D 99/00* (2006.01)
(Continued)

(52) U.S. Cl.
CPC ............ *G16H 40/20* (2018.01); *A61D 99/00* (2013.01); *G06F 3/167* (2013.01); *G06Q 30/04* (2013.01);
(Continued)

(58) Field of Classification Search
None
See application file for complete search history.

(56) References Cited

U.S. PATENT DOCUMENTS

2012/0179293 A1* 7/2012 Feingold ............... G16H 10/40
901/50
2012/0330555 A1 12/2012 Shaanan et al.
(Continued)

OTHER PUBLICATIONS

Lynch DT, Hall J, Foucar K. How I investigate monocytosis. Int J Lab Hematol. 2018;40:107-14. (Year: 2018).*
(Continued)

*Primary Examiner* — Jonathan Ng
(74) *Attorney, Agent, or Firm* — McDonnell Boehnen Hulbert & Berghoff LLP (57) ABSTRACT

An example method includes receiving a first order to conduct a first diagnostic test of a sample from a patient, sending the first order to the first diagnostic testing instrument for input into a queue of the first diagnostic testing instrument, receiving alerts and status of the diagnostic test as testing is performed and for indication of completion of the first diagnostic test, sending the alerts and status of the diagnostic test to a second computing device for notice to a technician, receiving an output of the first diagnostic test, generating a recommendation of follow-on testing to perform based on the output of the first diagnostic test, receiving confirmation to perform the follow-on testing, generating a second order to conduct a second diagnostic test of another sample from the patient, and sending the second order to the second diagnostic testing instrument for input into a queue for the second diagnostic testing instrument.

19 Claims, 5 Drawing Sheets

(51) Int. Cl.
  *G06F 3/16*   (2006.01)
  *G06Q 30/04*  (2012.01)
  *G16H 10/40*  (2018.01)
  *G16H 10/60*  (2018.01)
  *G16H 40/40*  (2018.01)
  *G16H 40/67*  (2018.01)
  *G16H 50/20*  (2018.01)
  *G16H 50/70*  (2018.01)

(52) U.S. Cl.
  CPC ............ *G16H 10/40* (2018.01); *G16H 10/60* (2018.01); *G16H 40/40* (2018.01); *G16H 40/67* (2018.01); *G16H 50/20* (2018.01); *G16H 50/70* (2018.01)

(56) References Cited

U.S. PATENT DOCUMENTS

| | | | |
|---|---|---|---|
| 2014/0122106 A1* | 5/2014 | Malven | G06Q 10/10 705/2 |
| 2014/0129172 A1 | 5/2014 | Eberhardt et al. | |
| 2016/0321414 A1* | 11/2016 | Salganicoff | G06N 20/00 |
| 2019/0355481 A1* | 11/2019 | Lamb | G16H 50/30 |
| 2020/0243171 A1* | 7/2020 | Schmidt | G16H 50/20 |
| 2020/0303066 A1* | 9/2020 | Bowers | G06Q 10/06316 |
| 2022/0044810 A1* | 2/2022 | D'Augustine | G16H 15/00 |
| 2023/0083600 A1* | 3/2023 | Snyder, Md | A61P 7/06 435/7.1 |

OTHER PUBLICATIONS

Favaloro, E. Contemporary platelet function testing. Clin Chem Lab Med 2010;48(5):579-598 (Year: 2010).*

Novis, David. "Reducing errors in the clinical laboratory: a lean production system approach".https://davidnovis.com/wp-content/uploads/2014/03/Lab-Med-Lean-Errors.pdf. Laboratory Medicine. 2008 (Year: 2008).*

International Search Report and Written Opinion prepared by the European Patent Office in International Application No. PCT/US2020/062677, mailed Mar. 3, 2021.

* cited by examiner

SYSTEMS, DEVICES, AND METHODS FOR MANAGING OPERATION OF DIAGNOSTIC TESTING INSTRUMENTS

CROSS-REFERENCE TO RELATED APPLICATION

The present disclosure claims priority to U.S. provisional patent application No. 62/943,587 filed on Dec. 4, 2019, the entire disclosure of which is hereby incorporated by reference.

FIELD

The present disclosure relates generally to methods for diagnostic instrument workflow, and more particularly, to controlling diagnostic instruments via a communication channel through a two-way laboratory hub and providing recommendations of follow-on testing to perform.

BACKGROUND

Many veterinary clinics have in-house diagnostic facilities capable of performing testing on site. A patient visiting the clinic can be evaluated by a veterinarian, and if needed, a sample can be taken for testing. Typically, a patient is seen in an examination room, and testing is performed by diagnostic equipment located in a separate area of the clinic.

The veterinary clinics can become very busy with multiple patients being scheduled for examination, and multiple diagnostic testing required to be performed. In these situations, veterinary staff needs real-time status updates and alerts for diagnostics wherever the individuals are located in the clinic, even when their hands are occupied, so as to operate efficiently and assist with diagnosing and treating the patients.

Accordingly, a more effective system is needed for providing real-time notifications of statuses throughout the clinic in a way that does not affect customer or patient workflows.

SUMMARY

In an example, a method is described comprising receiving a first order at a central computing device to conduct a first diagnostic test of a sample from a patient. The central computing device is in communication with a plurality of diagnostic testing instruments and the first diagnostic test is associated with a first diagnostic testing instrument and the first diagnostic testing instrument is one of the plurality of diagnostic testing instruments. Each of the diagnostic testing instruments of the plurality of diagnostic testing instruments may either include a queue for executing received orders and/or orders can be queued by the central computing device. The method also comprises sending, by the central computing device, the first order to the first diagnostic testing instrument for input into a queue for the first diagnostic testing instrument, and receiving, from the first diagnostic testing instrument, alerts and status of the diagnostic test as testing is performed and for indication of completion of the first diagnostic test. The method also comprises sending, by the central computing device, the alerts and status of the diagnostic test to a second computing device for notice to a technician, and receiving, from the first diagnostic testing instrument, an output of the first diagnostic test. The method also comprises generating a recommendation of follow-on testing to perform based on the output of the first diagnostic test, receiving confirmation to perform the follow-on testing, and generating a second order by the central computing device to conduct a second diagnostic test of another sample from the patient. The second diagnostic test is associated with a second diagnostic testing instrument and the second diagnostic testing instrument is one of the plurality of diagnostic testing instruments. The method also comprises sending, by the central computing device, the second order to the second diagnostic testing instrument for input into a queue for the second diagnostic testing instrument.

In another example, a central computing device is described that comprises one or more processors, and non-transitory computer readable medium having stored therein instructions that when executed by the one or more processors, causes the central computing device to perform functions. The functions comprise receiving a first order to conduct a first diagnostic test of a sample from a patient. The central computing device is in communication with a plurality of diagnostic testing instruments and the first diagnostic test is associated with a first diagnostic testing instrument and the first diagnostic testing instrument is one of the plurality of diagnostic testing instruments. Each of the diagnostic testing instruments of the plurality of diagnostic testing instruments includes either a queue for executing received orders and/or orders can be queued by the central computing device. The functions also comprise sending the first order to the first diagnostic testing instrument for input into a queue for the first diagnostic testing instrument, receiving, from the first diagnostic testing instrument, alerts and status of the diagnostic test as testing is performed and for indication of completion of the first diagnostic test, and sending the alerts and status of the diagnostic test to a second computing device for notice to a technician. The functions also comprise receiving, from the first diagnostic testing instrument, an output of the first diagnostic test, optionally generating a recommendation of follow-on testing to perform based on the output of the first diagnostic test, receiving confirmation to perform the follow-on testing, and generating a second order to conduct a second diagnostic test of another sample from the patient. The second diagnostic test is associated with a second diagnostic testing instrument and the second diagnostic testing instrument is one of the plurality of diagnostic testing instruments. The functions also comprise sending the second order to the second diagnostic testing instrument for input into a queue for the second diagnostic testing instrument.

In another example, a voice interactive veterinary system is described that comprises at least one veterinary analyzer to conduct a diagnostic test of a sample of a patient, and at least one two-way laboratory hub in communication with the at least one veterinary analyzer. The at least one two-way laboratory hub is operable to control operation of the at least one veterinary analyzer. The system also comprises means for controlling the at least one veterinary analyzer by voice communication via at least one voice-controlled device. The at least one voice-controlled device is in communication with the at least one two-way laboratory hub and the at least one voice-controlled device receives a voice command and the voice command is transmitted to the at least one veterinary analyzer via the at least one two-way laboratory hub.

The features, functions, and advantages that have been discussed can be achieved independently in various examples or may be combined in yet other examples.

Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Veterinary technicians are constantly multi-tasking in a clinic working directly with clients, patients, doctors, and different diagnostic hardware and software platforms. Examination rooms and diagnostic systems can be spread throughout the clinic, which means that the veterinary technician must physically revisit each system to check on patient orders. The systems and methods described herein provide a solution to enable veterinary technicians to unify different systems and data streams output by the system, and to provide a single, real-time status notification service to the veterinary technician that may be received on a mobile phone, a wearable device, or through another computing device located in the clinic.

The clinic can include a central computing device that is configured to manage, control, and operate diagnostic instruments. The central computing device can receive orders to conduct diagnostic tests of a sample from a patient, and send the orders to appropriate diagnostic testing instruments for input into a respective queue of the diagnostic testing instruments. The central computing device can also receive alerts and status of the diagnostic test as testing is performed, and provide the real-time alert and status notification service to the veterinary technician. The central computing device can further receive an output of the diagnostic tests, generate a recommendation of follow-on testing to perform based on the output of the diagnostic tests, and upon receiving confirmation to perform the follow-on testing the central computing device can generate a second order to conduct a second diagnostic test of another sample from the patient on another diagnostic testing instrument. The recommendations can be results-based suggested diagnosis, suggestions and information for follow-on testing to perform, and/or ordering inventory items for instrumentations as well.

Implementations of this disclosure provide technological improvements that are particular to computer technology, for example, those concerning operation and control of diagnostic instruments in the clinic. Computer-specific technological problems, such as receiving status updates of testing, can be wholly or partially solved by implementations of this disclosure. For example, implementation of this disclosure allows for veterinary technicians to be notified of status updates of testing, which can be very helpful in instances in which a diagnostic instrument requires user input for completion of the test. Rather than having the test sit idle until the veterinary technician returns to the testing room to receive results, the test can be continued following notification to the veterinary technician.

The systems and methods of the present disclosure further address problems particular to computer devices and operation of diagnostic instruments, for example, those concerning scheduling of the additional operation of further diagnostic instruments as a result of follow-on testing. A clinic generally includes many diagnostic instruments, and many patients may visit the clinic at any given time. Thus, scheduling of testing to be performed by the diagnostic instruments in a manner that is efficient and takes into account all patients needs and schedules is needed. Implementations of this disclosure can thus introduce new and efficient improvements in the ways in follow-on testing is scheduled by the central computing device for use of the diagnostic instruments in an efficient manner.

Figure 1:
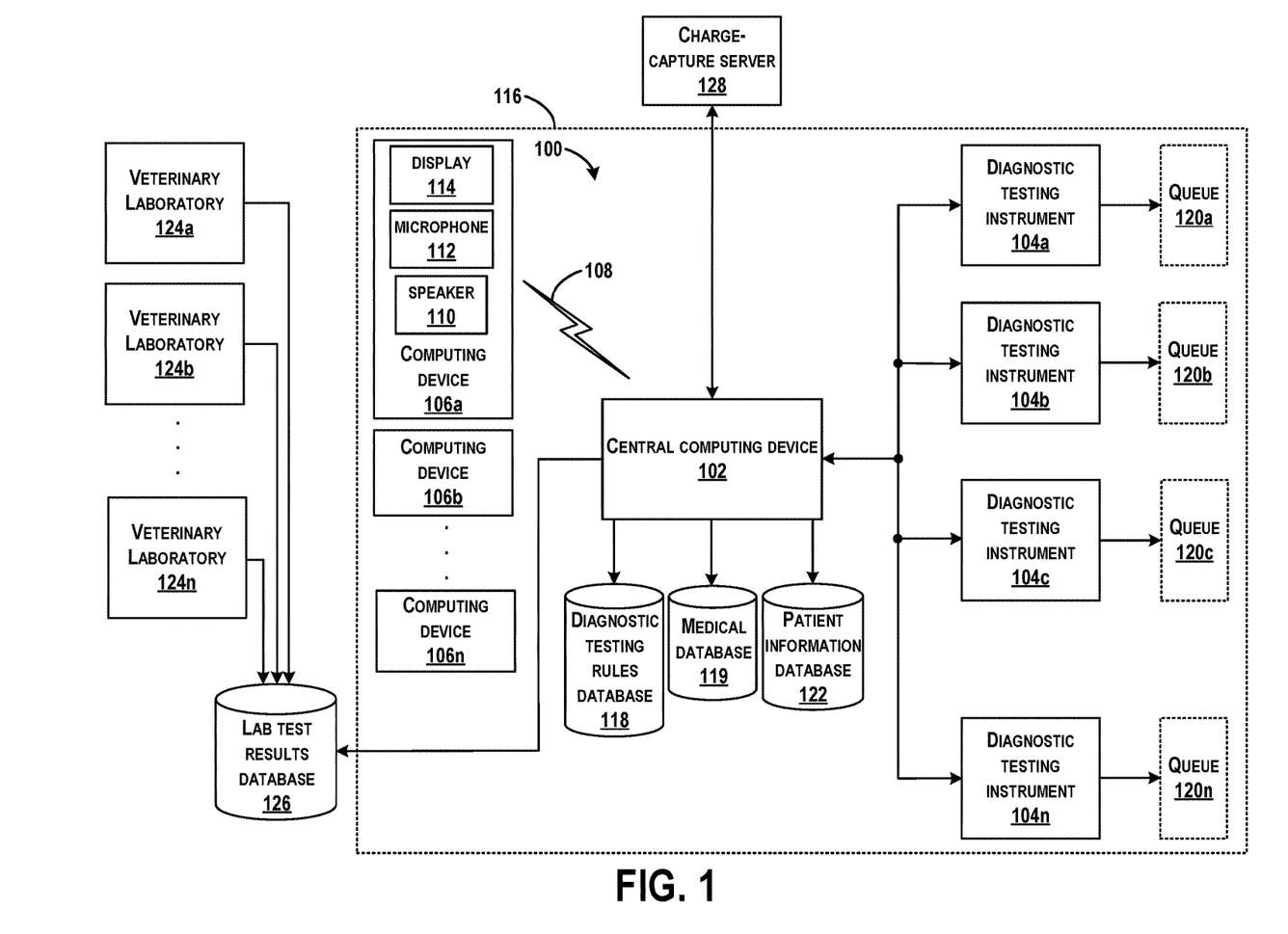
FIG. 1 illustrates an example of a system, according to an example implementation.

Referring now to the figures, FIG. 1 illustrates an example of a system 100, according to an example implementation. The system 100 includes a central computing device 102 coupled to and in communication with a plurality of diagnostic testing instruments 104*a-n*. The central computing device 102 may be in wired or wireless communication with the plurality of diagnostic testing instruments 104*a-n* (e.g., some may be in wired Ethernet communication and others may use Wi-Fi communication), and although not shown, the system 100 may further include, or components of the system 100 may be in communication with, a network (e.g., Internet) for access to cloud databases. Although four diagnostic testing instruments are shown, more or fewer diagnostic testing instruments may be included in the system 100.

The system 100 also includes computing devices 106*a-n* coupled to and in communication with the central computing device 102. The central computing device 102 may be in wired or wireless communication with the computing devices 106*a-n* (e.g., some may be in wired Ethernet communication and others may use Wi-Fi communication). FIG. 1 illustrates a wireless communication channel 108 between the computing device 106*a* and the central computing device 102, for example. Although three computing devices are shown, more or fewer computing devices may be included in the system 100.

The central computing device 102 may be a two-way laboratory hub (more details of the central computing device 102 are described with reference to FIG. 2), and the diagnostic testing instruments 104a-n may be veterinary analyzers operable to conduct a diagnostic test of a sample of a patient. The central computing device 102 is in communication with the veterinary analyzer and is operable to control operation of the veterinary analyzer. Within examples, the diagnostic testing instruments 104a-n may be any one or combination of a clinical chemistry analyzer, a hematology analyzer, a urine analyzer, an immunoassay reader, a sediment analyzer, a blood analyzer, and a digital radiology machine.

The computing devices 106a-n may be voice-controlled devices. In FIG. 1, the computing device 106a is shown to include a speaker 110, a microphone 112, and a display 114. Any of the computing devices 106a-n may include such components, or may include more or fewer components as well. For instance, the computing devices 106a-n may also include one or more processors, and data storage storing instructions executable by the one or more processors to perform functions as described herein by the computing devices 106a-n. The computing devices 106a-n may further include means for communicating with the central computing device 102, such as a receiver and transmitter for WiFi communication, and a network port for wired communication, for example. The computing devices 106a-n may all be the same or may be different types of devices. Examples types of devices for the computing devices 106a-n include a laptop or desktop computer, a mobile phone, a smart-speaker, a wearable device (e.g., smart watch), smart-display, or any type of device with reception and transmission means. The computing devices 106a-n may be positioned throughout a veterinary laboratory, for example.

In some examples, the system 100 is a voice interactive veterinary system including means for controlling the diagnostic testing instruments 104a-n (e.g., veterinary analyzers) by voice communication via at least one voice-controlled device. The at least one voice-controlled device (e.g., any of computing devices 106a-n) is in communication with the at least one two-way laboratory hub (e.g., central computing device 102) and the at least one voice-controlled device receives a voice command and the voice command is transmitted to the veterinary analyzer (e.g., any of diagnostic testing instruments 104a-n) via the at least one two-way laboratory hub.

In this example, the computing device 106a receives a voice command at the microphone 112 and transmits the voice command to the central computing device 102 via the wireless communication channel 108. In this example, communications between the computing device 106a and the central computing device 102 are direct peer-to-peer communications. In other examples, communications between the computing device 106a and the central computing device 102 can be performed through a network.

Once received, the central computing device 102 then transmits the voice command to any of diagnostic testing instruments 104a-n, as appropriate, for controlling operation of the diagnostic testing instruments 104a-n. The diagnostic testing instruments 104a-n can output a status of operation to the central computing device 102, which sends a status notification to the computing devices 106a-n. The diagnostic testing instruments 104a-n can also output error signals or other information to the central computing device 102, which sends an alert notification to the computing devices 106a-n. In one example, the computing device 106a includes a means for activating the speaker 110 (e.g., processor executing instructions stored in storage as described below) to announce the alerts and status of any of the diagnostic testing instruments 104a-n.

In FIG. 1, the central computing device 102, the diagnostic testing instruments 104a-n, and the computing devices 106a-n are positioned in a veterinary laboratory 116. The computing devices 106a-n may be positioned throughout the veterinary laboratory 116, such as one in each room, and the central computing device 102 and the diagnostic testing instruments 104a-n may be positioned in the testing room. In this arrangement, a veterinary technician may schedule or control operation of the diagnostic testing instruments 104a-n via voice commands provided to any of the computing devices 106a-n, and thus, may do so while being present in any room of the veterinary laboratory 116. In addition, the veterinary technician can receive status updates and testing results of the diagnostic testing instruments 104a-n via speaker outputs of any of the computing devices 106a-n (e.g., such as speaker 110 of the computing device 106a).

The system 100 further includes a database 118 storing a plurality of rules for performing diagnostic testing, and the central computing device 102 (e.g., two-way laboratory hub) is in communication with the database 118 for access to the plurality of rules. In an example operation, one of the computing devices 106a-n can receive a test query, which is transmitted to the central computing device 102. In response, the central computing device 102 may access the database 118 to identify rules of the plurality of rules for performing diagnostic testing specific for the test query, and the central computing device 102 can send the rules of the plurality of rules for performing diagnostic testing specific for the test query to the specific computing device that received the test query for playout on a speaker. Thus, a veterinary technician is able to access the diagnostic testing rules database 118 via any of the computing devices 106a-n. Note that in some examples, the database 118 may reside in the cloud and the central computing device 102 can access the database 118 via a network.

The system 100 further includes a database 119 storing medical data including ranges of normal, low, and high test results, and the central computing device 102 (e.g., two-way laboratory hub) is in communication with the database 119 for access to the data. In an example operation, the central computing device 102 may access the database 119 to compare a current test result with the typical ranges for interpretation of the current test result, and the central computing device 102 can send an analysis of the current test result to the computing devices 106a-n for playout on a speaker. Thus, a veterinary technician is able to receive an analysis of the test results via any of the computing devices 106a-n. In some examples, the database 119 may reside in the cloud. In other examples, the database 119 may be included within the central computing device 102.

In another example operation, of the interactive veterinary system, any of the computing devices 106a-n is operable to receive a voice command that is indicative of a first order to conduct a first diagnostic test of a sample from a patient on one of the diagnostic testing instruments 104a-n. Each of the diagnostic testing instruments 104a-n includes a queue 120a-n for executing received orders or has the ability to be queued remotely, such as by the central computing device 102. Although FIG. 1 illustrates a specific queue for each instrument, not all diagnostic testing instruments 104a-n may themselves include or contain a queue. For such instruments that do not contain a queue, the central computing device 102 may control orders for the instruments and may include a queue for the specific instruments.

The queue 120a-n indicates, for each of the diagnostic testing instruments, a schedule or order by which testing is to be performed. As one example, the queue 120a-n indicates an order to conduct testing for different patients. The central computing device 102 can receive the first order from any of the computing devices 106a-n and send the first order to the corresponding diagnostic testing instrument, such as the diagnostic testing instrument 104a, for input into the queue 120a. The first order may include information as to a specific test to be performed and the patient information. The central computing device 102 selects the corresponding diagnostic testing instrument 104a from among the diagnostic testing instruments 104a-n that is appropriate for performing the specific test. If more than one of the diagnostic testing instruments 104a-n may perform the test (e.g., there are duplicate instruments in the veterinary laboratory 116), the central computing device 102 may send the first order to the diagnostic testing instrument with a fewest number of pending orders in its queue.

The central computing device 102 operates to control and manage the testing performed by the diagnostic testing instruments 104a-n. A veterinary technician will still place samples for testing on specific instruments; however, functionality of the diagnostic testing instruments 104a-n is controlled by the central computing device 102, and test results are sent back to the central computing device 102.

In some examples, some or all the diagnostic testing instruments 104a-n do not have user interfaces, and thus, the central computing device 102 is required to run the diagnostic testing instruments 104a-n. Also, the central computing device 102 may coordinate queuing of samples if the particular diagnostic testing device does not have on-board queuing capabilities.

In further examples, the central computing device 102 (i) receives an output of a diagnostic test performed by the diagnostic testing instruments 104a-n, (ii) generates a recommendation of follow-on testing to perform based on the output of the diagnostic test, and (iii) sends the recommendation to one or more of the computing devices 106a-n to announce the recommendation to a technician. The recommendation can be generated based on a number of factors including the output of the diagnostic test and historical test results of the patient. In this regard, in FIG. 1, the system 100 may also include a patient information database 122 (or Practice Information Management Software "PIMS" database) that stores and manages information related to a patient. Such information can include name, date of birth, address, sex, breed, and associated medical data (e.g., blood chemistry test results, hematology test results, infectious disease test results, non-infectious disease test results, urinalysis test results, cytology data, morphology data, radiology images, immunoassay test result images, and billing data etc.). The central computing device 102 can access the patient information database 122 to retrieve historical test results of the patient, and compare the historical test results to the current diagnostic test result so as to make a recommendation of any follow-up or follow-on testing that should be performed.

The central computing device 102 can receive outputs of a plurality of diagnostic tests performed by the plurality of diagnostic testing instruments 104a-n (or by any number of the diagnostic testing instruments 104a-n), and then generate the recommendation of the follow-on testing to perform based on all outputs received from any and all of the diagnostic tests. In this way, the central computing device 102 utilizes all available information to make recommendations of further testing to perform.

In some other examples, recommendations can be made using information from other laboratories. For example, the central computing device 102 and the diagnostic testing instruments 104a-n are positioned in the veterinary laboratory 116, and additional veterinary laboratories 124a-n also can be present that include the same or similar diagnostic testing instruments 104a-n. A lab test results database 126 may store diagnostic test results from all veterinary laboratories 124a-n and 116, as well as associated information including symptoms and follow-on testing performed in each situation. The central computing device 102 may access the lab test results database 126 to learn what the other veterinary laboratories 124a-n have done in some instances and leverage success and failures of the other veterinary laboratories 124a-n when generating the recommendation for any follow-on testing.

Referring back to the operation of the system 100, after sending the recommendation to one or more of the computing devices 106a-n to announce the recommendation to a technician, the central computing device 102 will await receipt of any further instructions. Upon receipt of a second voice command by any of the computing devices 106a-n to follow the recommendation, which is subsequently sent to the central computing device 102, the central computing device 102 generates a second order to conduct a second diagnostic test of another sample from the patient and sends the second order to a second veterinary analyzer (another of the diagnostic testing instruments 104a-c) for input into a queue of the second veterinary analyzer.

As a specific example of recommendations and follow-on testing, consider a scenario where a patient has a urine test conducted on a diagnostic testing instrument and results show Proteinuria (USG<1.030 or protein >25 mg/dl). The central computing device 102 can receive the results and execute algorithms (from stored memory) to recommend running urine in the SediVue DX where it shows active sediment (WBC, RBC, bacteria). In addition, the central computing device 102 can generate recommendations to send a bacterial culture and run a susceptibility test at a reference lab. Here, the central computing device 102 provides the recommendation to the computing devices 106a-n so that alerts can be provided to lab technicians of possible follow-on testing to perform.

When a veterinary technician is scheduling orders using voice commands, the voice commands received by any of the computing devices 106a-n are generally indicative of instructions to modify respective queues for the diagnostic testing instruments 104a-n, and the central computing device 102 transmits the instructions to modify the respective queues of the diagnostic testing instruments 104a-n. The respective queues 120a-n, in some examples, may only be modifiable via the central computing device 102.

Thus, the system 100 can provide alerts and status information, interpretation or test results, as well as recommendation information to be communicated from the diagnostic testing instruments 104a-n to the central computing device 102, and then to the computing devices 106a-n. Veterinary technician located in vicinity of the computing devices 106a-n will be able to hear the information, and take appropriate action. In an example workflow, a veterinary technician may schedule a test via voice command, and then go to the diagnostic testing instrument 104a to input the sample for testing. Once input, the test may begin and the veterinary technician can complete other tasks. Once the test is completed, a status notification is sent from the diagnostic testing instrument 104a to the central computing device 102, which transmits the status notification to all the computing devices 106a-n for announcing the status. The veterinary technician may hear the status and then return to the diagnostic testing instrument 104a to retrieve the sample and obtain the test results.

If a runtime error is experienced by the diagnostic testing instrument 104a, an error message is sent to the central computing device 102, which generates an alert message to be sent to the computing devices 106a-n and broadcast by the computing devices 106a-n.

In one example, runtime errors may be experienced by the diagnostic testing instruments 104a-n. Example runtime errors include a slide failure or a missing pipette tip on the analyzer. In this instance, the diagnostic testing instruments 104a-n can be programmed to send a message to the central computing device 102 informing of the pending runtime error, and the central computing device 102 can send a notification message to the computing devices 106a-n. The lab technician can then receive an alert via the computing devices 106a-n with a message indicating the errors so that the errors can be addressed quickly rather than having the machines remain idle with no knowledge of the errors.

Another example runtime error includes platelet clumping or insufficient platelet count on a test sample. When this occurs, the diagnostic testing instrument may pause testing or provide incomplete results. A technician may be required to re-run the test in this instance, and rather than having the testing remain idle, the runtime error can be broadcast to the lab technician via the computing devices 106a-n.

FIG. 1 also illustrates a charge-capture server 128 coupled to and in communication with the central computing device 102. The charge-capture server 128 may receive from the central computing device 102 information indicative of the different diagnostic tests that are performed for indexing into a record for the patient. The charge-capture server 128 can operate to coordinate billing information, and integrate testing into the billing system so that invoices are organized and completed.

In FIG. 1, the central computing device 102 is in communication with many components, and the communication may be wired or wireless communications, and the communication may be direct (peer-to-peer) or over a network (not shown) as well.

Figure 2:
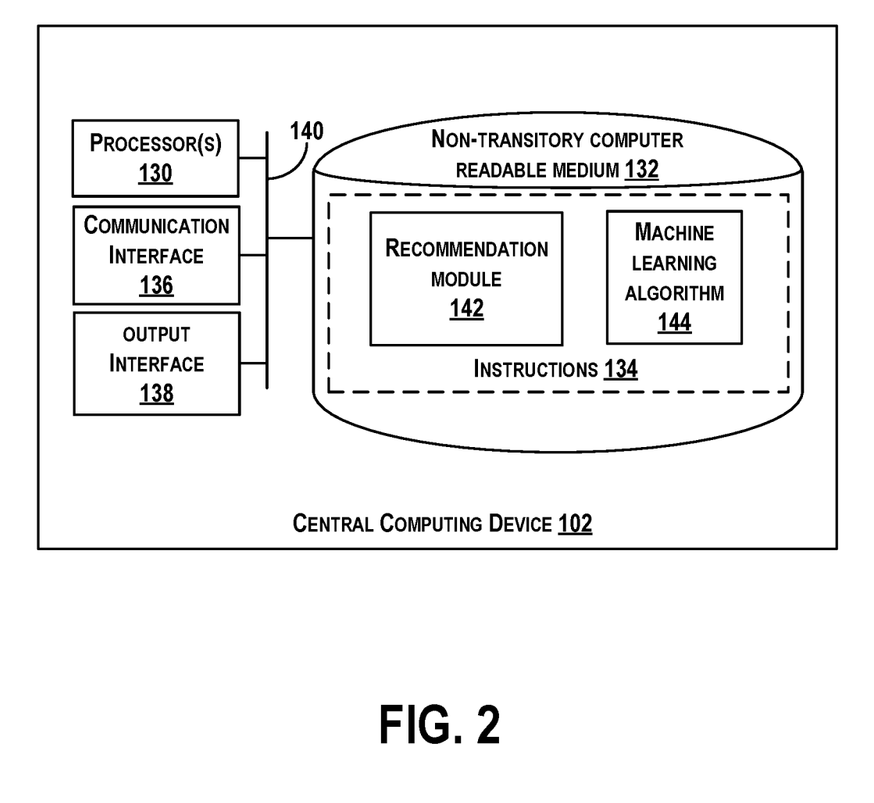
FIG. 2 illustrates an example of the central computing device, according to an example implementation.

FIG. 2 illustrates an example of the central computing device 102, according to an example implementation. The central computing device 102 includes one or more processor(s) 130, and non-transitory computer readable medium 132 having stored therein instructions 134 that when executed by the one or more processor(s) 130, causes the central computing device 120 to perform functions for operation, management, and control of diagnostic instruments.

To perform these functions, the central computing device 102 also includes a communication interface 136, an output interface 138, and each component of the central computing device 102 is connected to a communication bus 140. The central computing device 102 may also include hardware to enable communication within the central computing device 102 and between the central computing device 102 and other devices (not shown). The hardware may include transmitters, receivers, and antennas, for example. The central computing device 102 may further include a display (not shown).

The communication interface 136 may be a wireless interface and/or one or more wireline interfaces that allow for both short-range communication and long-range communication to one or more networks or to one or more remote devices. Such wireless interfaces may provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 136 may be configured to receive input data from one or more devices, and may also be configured to send output data to other devices.

The non-transitory computer readable medium 132 may include or take the form of memory, such as one or more computer-readable storage media that can be read or accessed by the one or more processor(s) 130. The non-transitory computer readable medium 132 can include volatile and/or non-volatile storage components, such as optical, magnetic, organic or other memory or disc storage, which can be integrated in whole or in part with the one or more processor(s) 130. In some examples, the non-transitory computer readable medium 132 can be implemented using a single physical device (e.g., one optical, magnetic, organic or other memory or disc storage unit), while in other examples, the non-transitory computer readable medium 132 can be implemented using two or more physical devices. The non-transitory computer readable medium 132 thus is a computer readable storage, and the instructions 134 are stored thereon. The instructions 134 include computer executable code.

The one or more processor(s) 130 may be general-purpose processors or special purpose processors (e.g., digital signal processors, application specific integrated circuits, etc.). The one or more processor(s) 130 may receive inputs from the communication interface 136 (e.g., x-ray images), and process the inputs to generate outputs that are stored in the non-transitory computer readable medium 132. The one or more processor(s) 130 can be configured to execute the instructions 134 (e.g., computer-readable program instructions) that are stored in the non-transitory computer readable medium 132 and are executable to provide the functionality of the central computing device 102 described herein.

The output interface 138 outputs information for transmission, reporting, or storage, and thus, the output interface 138 may be similar to the communication interface 136 and can be a wireless interface (e.g., transmitter) or a wired interface as well.

Within one example, in operation, when the instructions 134 are executed by the one or more processor(s) 130, the one or more processor(s) 130 are caused to perform functions including (i) receiving a first order to conduct a first diagnostic test of a sample from a patient, (ii) sending the first order to a first diagnostic testing instrument 104a for input into a queue 120a for the first diagnostic testing instrument 104a, (iii) receiving, from the first diagnostic testing instrument 104a, an output of the first diagnostic test, (iv) generating a recommendation of follow-on testing to perform based on the output of the first diagnostic test, (v) receiving confirmation to perform the follow-on testing, (vi) generating a second order to conduct a second diagnostic test of another sample from the patient, and (vii) sending the second order to the second diagnostic testing instrument 104b for input into a queue 120b for the second diagnostic testing instrument 104b. Thus, the instructions 134 are executable for creating an efficient workflow process in the veterinary laboratory 116, for example.

The instructions 134 may include specific software for performing the functions including a recommendation module 142 and a machine learning algorithm 144. The recommendation module 142 is executed to identify and determine appropriate recommendations for follow-on testing to provide based on any of a number of factors including the test results, historical test results, test results observed by other veterinary laboratories with patients in similar circumstances, etc. Alternatively, "recommendations" may comprise a list of testing options presented to the user.

The machine learning algorithm 144 uses statistical models to generate the recommendation of follow-on testing to perform effectively without using explicit instructions, but instead, by relying on patterns and inferences. In one example, the central computing device 102 receives outputs of diagnostic tests performed by diagnostic testing instruments positioned in a plurality of veterinary laboratories 124a-n by accessing the lab test results database 126, and uses the machine learning algorithm 144 to process the outputs of diagnostic tests performed by diagnostic testing instruments positioned in the plurality of veterinary laboratories 124a-n so as to identify patterns of outputs and associated follow-on testing performed. The central computing device 102 can then generate the recommendation of follow-on testing to perform based on the patterns of outputs and associated follow-on testing performed at the plurality of veterinary laboratories 124a-n.

The machine learning algorithm 144 can utilize data in the lab test results database 126 as a knowledge base of training data to learn of symptoms and test results for which certain follow-on testing was performed, and to learn if the follow-on testing was successful.

The machine learning algorithm 144 can thus operate according to machine learning tasks as classified into several categories. In supervised learning, the machine learning algorithm 144 builds a mathematical model from a set of data that contains both the inputs and the desired outputs. The set of data is sample data known as the "training data", in order to make predictions or decisions without being explicitly programmed to perform the task. For example, for determining a recommendation for a follow-on urine test, the training data for a supervised learning algorithm would include diagnostic test results (perhaps in a range of values) that resulted in urine tests being a recommended next step.

In another category referred to as semi-supervised learning, the machine learning algorithm 144 develops mathematical models from incomplete training data, where a portion of the sample input does not have labels. A classification algorithm can then be used when the outputs are restricted to a limited set of values.

In another category referred to as unsupervised learning, the machine learning algorithm 144 builds a mathematical model from a set of data that contains only inputs and no desired output labels. Unsupervised learning algorithms are used to find structure in the lab test results database 126, such as grouping or clustering of data points. Unsupervised learning can discover patterns in data in the lab test results database 126, and can group the inputs into categories.

Alternative machine learning algorithms may be used to learn and classify types of follow testing to consider for generating the recommendations, such as deep learning though neural networks or generative models. Deep machine learning may use neural networks to analyze prior test results through a collection of interconnected processing nodes. The connections between the nodes may be dynamically weighted. Neural networks learn relationships through repeated exposure to data and adjustment of internal weights. Neural networks may capture nonlinearity and interactions among independent variables without pre specification. Whereas traditional regression analysis requires that nonlinearities and interactions be detected and specified manually, neural networks perform the tasks automatically.

Still other machine learning algorithms or functions can be implemented to generate the recommendations, such as any number of classifiers that receives input parameters and outputs a classification (e.g., attributes of the image). Support vector machine, Bayesian network, a probabilistic boosting tree, neural network, sparse auto-encoding classifier, or other known or later developed machine learning algorithms may be used. Any semi-supervised, supervised, or unsupervised learning may be used. Hierarchal, cascade, or other approaches may be also used.

The machine learning algorithm 144 may thus be considered an application of rules in combination with learning from prior data to identify appropriate recommendations for follow-on testing to recommend. Analyzing prior data allows the machine learning algorithm 144 to learn patterns of test results and follow-on testing that is generally performed when such test results are observed, for example.

In operation, the central computing device 102 generally synchronizes, organizes, and displays PIMS data, veterinary diagnostic testing instrument data and/or status, and veterinary diagnostic testing workflows. The central computing device 102 further controls operation of the diagnostic testing instruments 104a-n, and operates as a user interface for the diagnostic testing instruments 104a-n.

Figure 3:
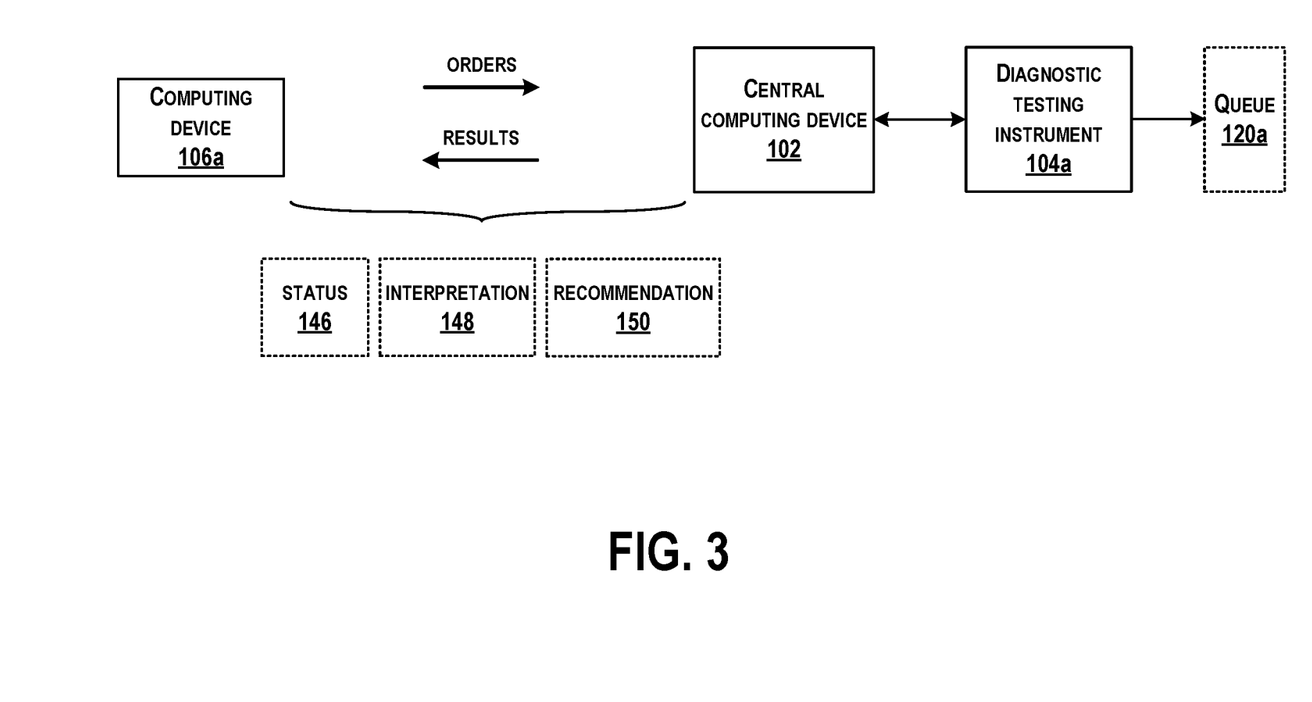
FIG. 3 illustrates a portion of the system of FIG. 1 and sample workflow processes, according to an example implementation.

FIG. 3 illustrates a portion of the system of FIG. 1 and sample workflow processes, according to an example implementation. The central computing device 102 and the computing device 106a exchange different types of information that may be classified as status 146, interpretation 148, and recommendation 150. The status 146 information may include order and result status questions and responses, order and run status, and push notifications for orders and results. An order generally includes a request for performing a diagnostic test, and a result generally includes a test result.

The interpretation 148 information may include single and multiple result analysis, prescriptive result analysis, and context relevant observations (e.g., historical results). The interpretation 148 may be determined from considering the test results from a single diagnostic testing instrument or considering multiple test results from multiple diagnostic testing instruments.

The recommendation 150 information may include suggested additional diagnostic orders, sample preparation help for orders, and artificial intelligence or machine learning recommendations based on testing patterns.

As an example workflow in the veterinary laboratory 116, for a status query, a veterinary technician may provide a voice command or query to the computing device 106a including "what is the current status of Garfield?", where Garfield is a name of a patient being treated. The computing device 106a forwards the voice command to the central computing device 102, which checks the records to determine what tests have been performed on any samples taken from Garfield. The central computing device 102 finds that a urinalysis test was ordered and performed for Garfield. The central computing device 102 returns the status of the tests to the computing device 106a, which may announce via the speaker 110 that "Garfield's urinalysis results finished 5 minutes ago."

Following, the veterinary technician may request the interpretation 148 of the test results by providing a voice command to the computing device 106a including "interpret Garfield's results." The computing device 106a sends the new voice command to the central computing device 102, which can access the medical database 119 to analyze the test results. Note that in one example, processing of the commands can occur in cloud services and the medical database 119 may reside on the cloud. The services will then send the computations to the central computing device 102. The cloud services may execute AI/Recommendation Engines and include a stored comprehensive set of results/orders.

The central computing device 102 can send the analysis to the computing device 106a, which may announce via the speaker 110 that "Garfield's white blood cell count is high which may indicate infection. Would you like to hear our recommendation?" Upon receipt of a voice command, such as "yes", received at the computing device 106a and transmitted to the central computing device 102, the central computing device 102 may generate the recommendation for follow-on testing to be performed for assisting with a diagnosis. The central computing device 102 can send the recommendation to the computing device 106a, which may announce via the speaker 110 the following: "recommend running a urine sediment to confirm the presence of infection. Would you like me to add SediVue Dx to Garfield's order?" Upon receipt of a voice command, such as "yes", received at the computing device 106a and transmitted to the central computing device 102, the central computing device 102 may then generate a second order to conduct a second diagnostic test of another sample from the patient and send the second order to the diagnostic testing instrument for input into a queue of the diagnostic testing instrument. The central computing device 102 may also provide an acknowledgement, which is sent to the computing device 106a for playout on the speaker 110, such as "Ok, I've added a SediVue Dx to Garfield's order."

As another example workflow in the veterinary laboratory 116, for an interpretation query, a veterinary technician may provide a voice command or query to the computing device 106a including "what sample do I need for Scooby?", where Scooby is a name of a patient being treated. The computing device 106a forwards the voice command to the central computing device 102, which checks the records to determine what tests have been ordered and scheduled for Scooby. The central computing device 102 finds that a hematology and chemistry test was ordered. The central computing device 102 returns information indicating items needed to perform these tests to the computing device 106a, which may announce via the speaker 110 that "Scooby is having hematology and chemistry testing. You need a purple top and red top tube with 3 milliliters in each."

Based on testing conducted, other types of recommendation 150 may be provided. An interpretation 148 of a test may be indicative of platelet aggregate detected, resulting in the recommendation 150 being to confirm test results with a dot plot and/or blood film review. In instances where the interpretation 148 of a red blood cell run are indicative of non-regenerative anemia, the recommendation 150 provided can include to consider pre-regenerative anemia. Where the interpretation 148 of a red blood cell run are indicative of decreased iron availability, the recommendation provided can include to consider inflammation, iron deficiency, PSS, or breed-related microcytosis. Where the interpretation 148 of a white blood cell run are indicative of monocytosis, the recommendation 150 provided can include to consider inflammation (if lymphopenia consider glucocorticoid response). Still many other recommendations are possible based on the testing conducted, for example.

These example workflows illustrate only a few types of interactions between the computing device 106 and the central computing device 102. Of course, many other interactions are possible, and the systems, devices, and methods described herein provide beneficial improvements in the diagnostic workflow in the veterinary laboratory 116 for testing and recommendations for diagnosis. The interaction with the system 100 is hands free and eliminates a need for the veterinary technician to repeatedly visit diagnostic platforms to check and modify a patient's order. Additional benefits are provided via results interpretation and constructing recommendations and conversations based on patterns that the central computing device 102 can identify in the result data.

Figure 4:
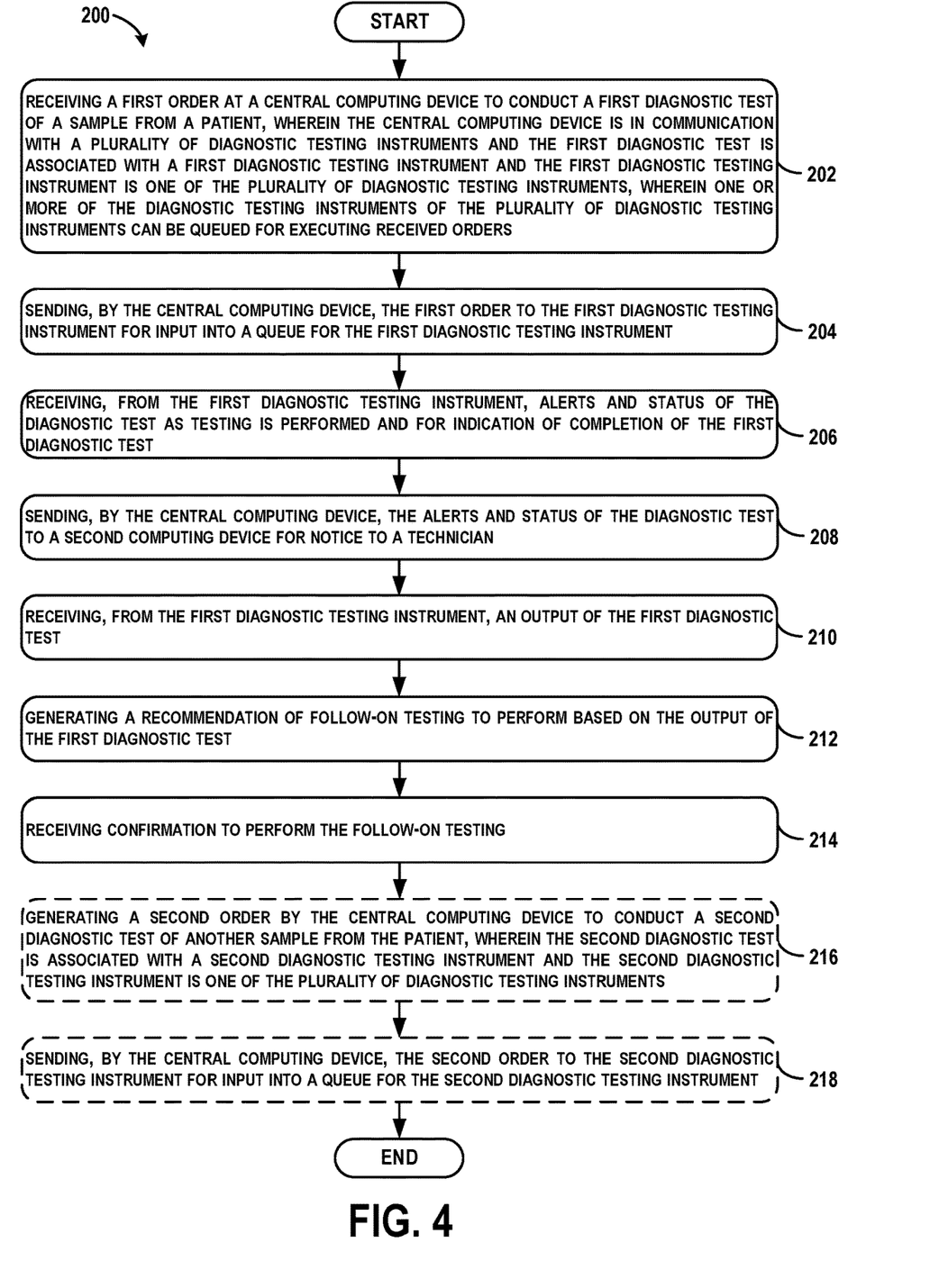
FIG. 4 shows a flowchart of another example of a method for a managing operation of diagnostic testing instruments, according to an example implementation.

FIG. 4 shows a flowchart of another example of a method 200 for a managing operation of diagnostic testing instruments, according to an example implementation. Method 200 shown in FIG. 4 presents an example of a method that could be used with the system 100 shown in FIG. 1 or the central computing device 102 shown in FIG. 1, for example. Further, devices or systems may be used or configured to perform logical functions presented in FIG. 4. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-218. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 4, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 202, the method 200 includes receiving a first order at a central computing device 102 to conduct a first diagnostic test of a sample from a patient, and the central computing device 102 is in communication with a plurality of diagnostic testing instruments 104a-n and the first diagnostic test is associated with a first diagnostic testing instrument 104a and the first diagnostic testing instrument is one of the plurality of diagnostic testing instruments 104a-n. One or more of the diagnostic testing instruments of the plurality of diagnostic testing instruments 104a-n can be queued (e.g., includes a queue 120a-n) for executing received orders.

At block 204, the method 200 includes sending, by the central computing device 102, the first order to the first diagnostic testing instrument 104a for input into a queue 120a for the first diagnostic testing instrument 104a.

At block 206, the method 200 includes receiving, from the first diagnostic testing instrument, alerts and status of the diagnostic test as testing is performed and for indication of completion of the first diagnostic test;

At block 208, the method 200 includes sending, by the central computing device 102, the alerts and status of the diagnostic test to a second computing device 106a for notice to a technician.

At block 210, the method 200 includes receiving, from the first diagnostic testing instrument 104a, an output of the first diagnostic test. For example, the first diagnostic testing instrument 104 sends the output of the first diagnostic test to the central computing device 102 upon completion of the test.

At block 212, the method 200 includes optionally generating a recommendation of follow-on testing to perform based on the output of the first diagnostic test. For example, the central computing device 102 may generate the recommendation using the recommendation module 142 and/or the machine learning algorithm 144 as described above. The central computing device 102 may then send the recommendation to the computing devices 106a-n for playout on a speaker to a technician. In some examples, the central computing device 102 generates the recommendation of the follow-on testing to perform based on historical test results of the patient. In other examples, the central computing device 102 receiving outputs of a plurality of diagnostic tests performed by the plurality of diagnostic testing instruments 104a-n, and generates the recommendation of the follow-on testing to perform based on the outputs of the plurality of diagnostic tests.

In some examples, the recommendation module 142 of the central computing device 102 includes a rules-based engine that is executed to generate the recommendation. The rules include mappings of ranges of test results to a second complimentary test to be performed so as to confirm a diagnosis or assist with a diagnosis, for example.

In some examples, the recommendation module 142 of the central computing device 102 can provide recommendations for testing on instruments or equipment that is not present in the veterinary laboratory 116. For example, the central computing device 102 may determine that a hematology analysis is a next recommendation test to perform, and that the veterinary laboratory 116 does not have a hematology analyzer as one of the diagnostic testing instruments 104a-n (e.g., a hematology analyzer is not connected or coupled to the central computing device 102). The central computing device 102 may then determine and recommend the test to be performed in a reference lab test (e.g., via access to cloud databases over the network). The central computing device 102 could therefore determine a reference lab capable of performing the recommended test, and determine a location of the reference lab as well, for input as the recommendation to the veterinary technician.

In addition, the central computing device 102 may need to account for recommending multiple test associated with "test codes" as there may be more than one test code, and some codes could span multiple testing modalities. For example, different test are associated with specific test codes, and the central computing device 102 may store such codes and associate a request for a test with a specific test code.

At block 214, the method 200 includes receiving confirmation to perform the follow-on testing. For example, a technician may provide a voice command as the confirmation, which is received by any one of the computing devices 106a-n and forwarded to the central computing device 102. Alternatively, follow-on testing may include a repeat run of a test already initiated, e.g. if one or more run-failure events are detected (i.e. insufficient sample, mechanical error, power interruptions, etc.).

At block 216, the method 200 includes optionally generating a second order by the central computing device 102 to conduct a second diagnostic test of another sample from the patient, and the second diagnostic test is associated with a second diagnostic testing instrument 104b and the second diagnostic testing instrument is one of the plurality of diagnostic testing instruments 104a-n. In some examples, conducting the second diagnostic test of another sample from the patient includes conducting the second diagnostic test using a second portion of the sample from the patient. In other examples, the sample is a first sample from the patient, and conducting the second diagnostic test using a second sample from the patient includes receiving a second sample from the patient that is taken from the patient at a different time from the first sample.

At block 218, the method 200 includes optionally sending, by the central computing device 102, the second order to the second diagnostic testing instrument 104b for input into a queue 120b for the second diagnostic testing instrument 104b.

Figure 5:
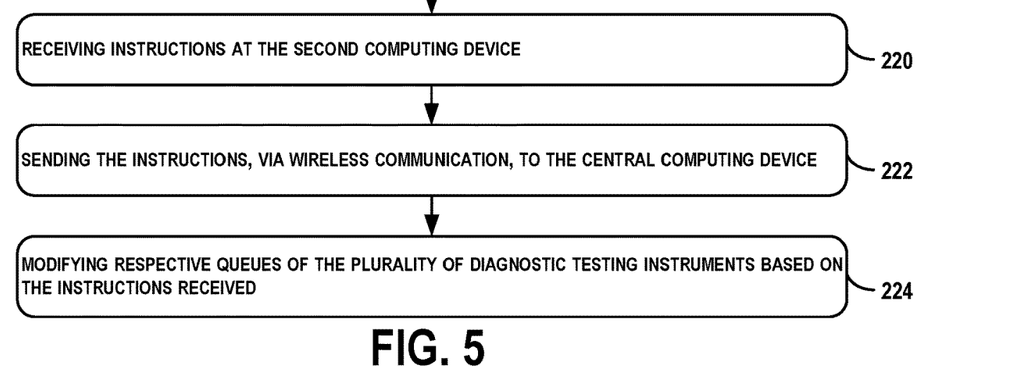
FIG. 5 shows a flowchart of additional functions that may be used with the method in FIG. 4, according to an example implementation.

FIG. 5 shows a flowchart of additional functions that may be used with the method 200 in FIG. 4, according to an example implementation. For example, at block 220, functions include receiving instructions at the second computing device 106a. At block 222, functions include sending the instructions, via a wireless communication channel 108, to the central computing device 102. At block 224, functions include modifying respective queues of the plurality of diagnostic testing instruments 104a-n based on the instructions received.

Figure 6:
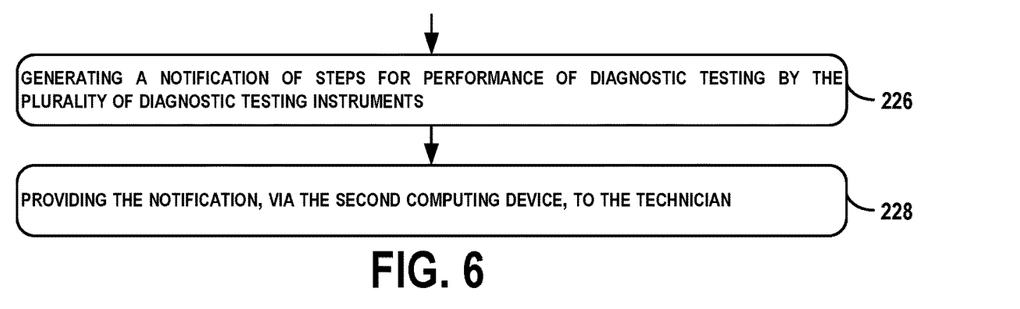
FIG. 6 shows a flowchart of additional functions that may be used with the method in FIG. 4, according to an example implementation.

FIG. 6 shows a flowchart of additional functions that may be used with the method 200 in FIG. 4, according to an example implementation. For example, at block 226, functions include generating a notification of steps for performance of diagnostic testing by the plurality of diagnostic testing instruments 104a-n. At block 228, functions include providing the notification, via the second computing device 106a, to the technician.

Figure 7:
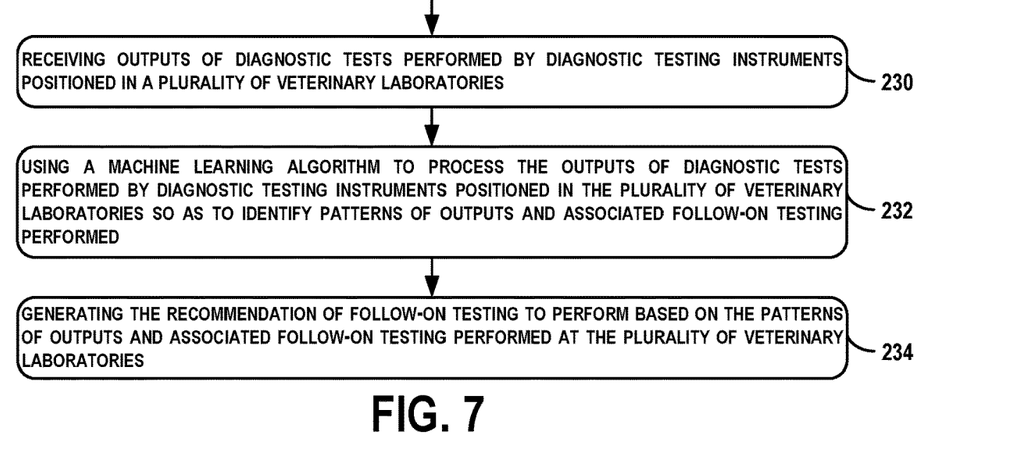
FIG. 7 shows a flowchart of additional functions that may be used with the method in FIG. 4, according to an example implementation.

FIG. 7 shows a flowchart of additional functions that may be used with the method 200 in FIG. 4, according to an example implementation. For example, the central computing device 102 and the plurality of diagnostic testing instruments 104a-n may be positioned in a first veterinary laboratory 116. At block 230, functions include receiving outputs of diagnostic tests performed by diagnostic testing instruments positioned in a plurality of veterinary laboratories 124a-n. At block 232, functions include using a machine learning algorithm 144 to process the outputs of diagnostic tests performed by diagnostic testing instruments positioned in the plurality of veterinary laboratories 124a-n so as to identify patterns of outputs and associated follow-on testing performed. At block 234, functions include generating the recommendation of follow-on testing to perform based on the patterns of outputs and associated follow-on testing performed at the plurality of veterinary laboratories 124a-n.

Figure 8:
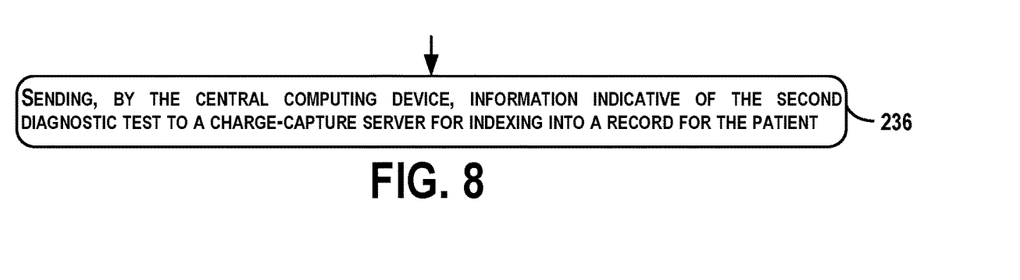
FIG. 8 shows a flowchart of additional functions that may be used with the method in FIG. 4, according to an example implementation.

FIG. 8 shows a flowchart of additional functions that may be used with the method 200 in FIG. 4, according to an example implementation. For example, at block 236, functions include sending, by the central computing device 102, information indicative of the second diagnostic test to a charge-capture server 128 for indexing into a record for the patient.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A computer-implemented method comprising:
   receiving a first order at a central computing device to conduct a first diagnostic test of a sample from a patient, wherein the central computing device is in communication with a plurality of diagnostic testing instruments and the first diagnostic test is associated with a first diagnostic testing instrument and the first diagnostic testing instrument is one of the plurality of diagnostic testing instruments, wherein one or more of the diagnostic testing instruments of the plurality of diagnostic testing instruments can be queued for executing received orders;
   sending, by the central computing device, the first order to the first diagnostic testing instrument for input into a queue for the first diagnostic testing instrument;
   the first diagnostic testing instrument executing received orders input into the queue by the central computing device and initiating the first diagnostic test of the sample from the patient including one of a blood chemistry test, a hematology test, or a urinalysis test;
   receiving, from the first diagnostic testing instrument, alerts and status of the first diagnostic test as testing is performed and for indication of completion of the first diagnostic test, wherein the alerts and status of the first diagnostic test include an indication of a pending runtime error in which the first diagnostic testing instrument remains idle due to testing being paused;
   sending, by the central computing device, the alerts and status of the first diagnostic test to a second computing device for notice to a technician, wherein the alerts and status of the first diagnostic test include an alert of the first diagnostic testing instrument requiring user input for completion of the first diagnostic test;
   the first diagnostic testing instrument continuing the first diagnostic test of the sample from the patient following receipt of the user input at the first diagnostic testing instrument;
   receiving, from the first diagnostic testing instrument, an output of the first diagnostic test;
   executing computer readable instructions by the central computing device to perform a rules-based engine, including mappings of ranges of test results to complimentary tests to be performed to confirm or assist with a diagnosis, to generate a recommendation of follow-on testing to perform based on the output of the first diagnostic test;
   receiving confirmation to perform the follow-on testing; and
   the central computing device scheduling of the follow-on testing to be performed by one or more of the plurality of diagnostic testing instruments by input into respective queues for the plurality of diagnostic testing instruments, wherein the scheduling occurs in an order based on (i) needs of a plurality of patients and (ii) a number of pending orders in the respective queues.

2. The method of claim 1, further comprising:
   generating a second order by the central computing device to conduct a second diagnostic test of another sample from the patient, wherein the second diagnostic test is associated with a second diagnostic testing instrument and the second diagnostic testing instrument is one of the plurality of diagnostic testing instruments; and
   sending, by the central computing device, the second order to the second diagnostic testing instrument for input into a queue for the second diagnostic testing instrument.

3. The method of claim 2, wherein generating the second order by the central computing device to conduct the second diagnostic test of another sample from the patient comprises generating the second order to conduct the second diagnostic test using a second portion of the sample from the patient.

4. The method of claim 2, wherein the sample is a first sample from the patient, and wherein generating the second order by the central computing device to conduct the second diagnostic test of another sample from the patient comprises generating the second order to conduct the second diagnostic test using a second sample from the patient, wherein the second sample is taken from the patient at a different time from the first sample.

5. The method of claim 2, further comprising:
sending, by the central computing device, information indicative of the second diagnostic test to a charge-capture server for indexing into a record for the patient.

6. The method of claim 1, further comprising:
receiving instructions at the second computing device;
sending the instructions, via wireless communication, to the central computing device; and
modifying respective queues of the plurality of diagnostic testing instruments based on the instructions received.

7. The method of claim 1, further comprising:
generating a notification of steps for performance of diagnostic testing by the plurality of diagnostic testing instruments; and
providing the notification, via the second computing device, to the technician.

8. The method of claim 1, wherein generating the recommendation of the follow-on testing to perform based on the output of the first diagnostic test further comprises generating the recommendation of the follow-on testing to perform based on historical test results of the patient.

9. The method of claim 1, further comprising:
receiving outputs of a plurality of diagnostic tests performed by the plurality of diagnostic testing instruments; and
wherein generating the recommendation of the follow-on testing to perform based on the output of the first diagnostic test further comprises generating the recommendation of the follow-on testing to perform based on the outputs of the plurality of diagnostic tests.

10. The method of claim 1, wherein the central computing device and the plurality of diagnostic testing instruments are positioned in a first veterinary laboratory, and the method further comprises:
receiving outputs of diagnostic tests performed by diagnostic testing instruments positioned in a plurality of veterinary laboratories;
using a machine learning algorithm to process the outputs of diagnostic tests performed by diagnostic testing instruments positioned in the plurality of veterinary laboratories so as to identify patterns of outputs and associated follow-on testing performed; and
generating the recommendation of follow-on testing to perform based on the patterns of outputs and associated follow-on testing performed at the plurality of veterinary laboratories.

11. The method of claim 1, further comprising:
generating the recommendation of the follow-on testing to perform including a urinalysis test result based on the output of the first diagnostic test being associated with a blood chemistry test result.

12. The method of claim 1, further comprising:
generating the recommendation of the follow-on testing to confirm the output of first diagnostic test with a dot plot and/or blood film review based on the output of the first diagnostic test being indicative of platelet aggregate detected.

13. The method of claim 1, further comprising:
generating the recommendation of the follow-on testing to consider pre-regenerative anemia based on the output of the first diagnostic test being indicative of non-regenerative anemia.

14. The method of claim 1, further comprising:
generating the recommendation of the follow-on testing to consider inflammation, iron deficiency, or breed-related microcytosis based on the output of the first diagnostic test being indicative of decreased iron availability.

15. The method of claim 1, further comprising:
generating the recommendation of the follow-on testing to consider inflammation based on the output of the first diagnostic test being indicative of monocytosis.

16. The method of claim 1, further comprising:
based on the follow-on testing to be performed by the one or more of the plurality of diagnostic testing instruments, generating information indicating items needed to perform the follow-on testing; and
providing the notification, via the second computing device, to the technician.

17. The method of claim 1, wherein the first order and the follow-on testing are associated with respective test codes, and the method further comprising:
the central computing device sending the respective test codes to a charge-capture server for indexing into a record for the patient.

18. The method of claim 1, further comprising:
generating a second order by the central computing device to conduct a second diagnostic test of another sample from the patient, wherein the second diagnostic test is associated with a second diagnostic testing instrument and the second diagnostic testing instrument is one of the plurality of diagnostic testing instruments; and
the central computing device scheduling of the second order by input into a queue for the second diagnostic testing instrument, wherein the scheduling occurs in an order based on (i) needs of a plurality of patients and (ii) a number of pending orders in the queue for the second diagnostic testing instrument.

19. A central computing device comprising:
one or more processors; and
non-transitory computer readable medium having stored therein instructions that when executed by the one or more processors, causes the central computing device to perform functions comprising:
receiving a first order to conduct a first diagnostic test of a sample from a patient, wherein the central computing device is in communication with a plurality of diagnostic testing instruments and the first diagnostic test is associated with a first diagnostic testing instrument and the first diagnostic testing instrument is one of the plurality of diagnostic testing instruments, wherein one or more of the diagnostic testing instruments of the plurality of diagnostic testing instruments can be queued for executing received orders;
sending the first order to the first diagnostic testing instrument for input into a queue for the first diagnostic testing instrument;
receiving, from the first diagnostic testing instrument, alerts and status of the first diagnostic test as testing is performed and for indication of completion of the first diagnostic test, wherein the alerts and status of the first diagnostic test include an indication of a pending runtime error in which the first diagnostic testing instrument remains idle due to testing being paused;
sending the alerts and status of the diagnostic test to a second computing device for notice to a technician, wherein the alerts and status of the first diagnostic test include an alert of the first diagnostic testing instrument requiring user input for completion of the first diagnostic test;

receiving, from the first diagnostic testing instrument, an output of the first diagnostic test following receipt of the user input at the first diagnostic testing instrument;

executing the instructions to perform a rules-based engine, including mappings of ranges of test results to complimentary tests to be performed to confirm or assist with a diagnosis, to generate a recommendation of follow-on testing to perform based on the output of the first diagnostic test;

receiving confirmation to perform the follow-on testing;

generating a second order to conduct a second diagnostic test of another sample from the patient, wherein the second diagnostic test is associated with a second diagnostic testing instrument and the second diagnostic testing instrument is one of the plurality of diagnostic testing instruments;

sending the second order to the second diagnostic testing instrument for input into a queue for the second diagnostic testing instrument; and scheduling of the second order to be performed by the second diagnostic testing instrument based on (i) needs of a plurality of patients and (ii) a number of pending orders in the queue for the second diagnostic testing instrument.

* * * * *